United States Patent
Cooper et al.

(10) Patent No.: US 9,511,344 B2
(45) Date of Patent: *Dec. 6, 2016

(54) ULTRAVIOLET LIGHT TREATMENT CHAMBER

(75) Inventors: James Randall Cooper, San Diego, CA (US); Richard May, San Diego, CA (US)

(73) Assignee: Ultraviolet Sciences, Inc., San Diego, CA (US)

( * ) Notice: Subject to any disclaimer, the term of this patent is extended or adjusted under 35 U.S.C. 154(b) by 802 days.

This patent is subject to a terminal disclaimer.

(21) Appl. No.: 11/959,445

(22) Filed: Dec. 18, 2007

(65) Prior Publication Data

US 2009/0155136 A1     Jun. 18, 2009

(51) Int. Cl.
*B01J 19/12* (2006.01)
*A61L 2/00* (2006.01)
(Continued)

(52) U.S. Cl.
CPC ............ *B01J 19/123* (2013.01); *A61L 2/0011* (2013.01); *A61L 2/0094* (2013.01); *A61L 9/015* (2013.01);
(Continued)

(58) Field of Classification Search
CPC ........ A61L 2/0011; A61L 9/015; A61L 9/205; A61L 2/0094; A61L 2209/212; B01J 19/123; B01J 19/124; B01J 2219/0877; C02F 1/325; C02F 2201/328; C02F 1/283; C02F 1/42; C02F 1/441; C02F 2201/003; C02F 2201/3223; A61M 1/3681; A61M 2205/053
(Continued)

(56) References Cited

U.S. PATENT DOCUMENTS 2,072,416 A    3/1937  Berndt et al.
2,072,417 A    3/1937  Berndt et al.
(Continued)

FOREIGN PATENT DOCUMENTS

DE        845497        7/1952
DE        19617467     11/1997
(Continued)

OTHER PUBLICATIONS

European Search Report for European App. No. 068014273 dated Nov. 19, 2009.
(Continued)

*Primary Examiner* — Xiuyu Tai
(74) *Attorney, Agent, or Firm* — Fitch, Even, Tabin & Flannery LLP (57) ABSTRACT

An apparatus for the treatment of a liquid comprising includes a chamber having at least one inner surface. The chamber is at least 80 percent enclosed. The apparatus also includes an ultraviolet (UV) transmissive tube and the UV transmissive tube disposed within the chamber and adapted for the passage of the liquid therethrough. The apparatus further includes an UV lamp and the UV lamp being disposed within the UV transmissive tube. A reflective material is interspersed between the chamber and the transmissive tube, and the reflective material is adapted so as to reflect at least a portion of light emitted by the UV lamp. Additionally, the reflective material is at least 80 percent reflective.

13 Claims, 6 Drawing Sheets

(51) Int. Cl.
*A61L 9/015* (2006.01)
*A61L 9/20* (2006.01)
*C02F 1/32* (2006.01)
*A61M 1/36* (2006.01)
*C02F 1/28* (2006.01)
*C02F 1/42* (2006.01)
*C02F 1/44* (2006.01)

(52) U.S. Cl.
CPC .............. *A61L 9/205* (2013.01); *B01J 19/124* (2013.01); *C02F 1/325* (2013.01); *A61L 2209/212* (2013.01); *A61M 1/3681* (2013.01); *A61M 2205/053* (2013.01); *B01J 2219/0877* (2013.01); *C02F 1/283* (2013.01); *C02F 1/42* (2013.01); *C02F 1/441* (2013.01); *C02F 2201/003* (2013.01); *C02F 2201/328* (2013.01); *C02F 2201/3223* (2013.01); *C02F 2201/3228* (2013.01)

(58) Field of Classification Search
USPC ...................................................... 422/186.3
See application file for complete search history.

(56) References Cited

U.S. PATENT DOCUMENTS

| | | |
|---|---|---|
| 2,482,507 A | 9/1949 | Rentschler et al. |
| 3,569,754 A | 3/1971 | Priebe et al. |
| 3,572,391 A | 3/1971 | Hirsch |
| 3,814,680 A | 6/1974 | Wood |
| 3,923,663 A * | 12/1975 | Reid ............................ 210/251 |
| 3,941,670 A | 3/1976 | Pratt |
| 3,959,504 A | 5/1976 | Grufstedt |
| 4,008,045 A | 2/1977 | Free |
| 4,042,325 A | 8/1977 | Tensmeyer |
| 4,042,850 A | 8/1977 | Ury et al. |
| 4,112,335 A | 9/1978 | Gonser |
| 4,141,686 A | 2/1979 | Lewis |
| 4,207,541 A | 6/1980 | Karger et al. |
| 4,232,276 A | 11/1980 | Iwata |
| 4,304,996 A | 12/1981 | Blades |
| 4,327,276 A | 4/1982 | Injushin et al. |
| 4,336,223 A | 6/1982 | Hillman |
| 4,400,270 A | 8/1983 | Hillman |
| 4,469,835 A | 9/1984 | Laurin |
| 4,507,587 A | 3/1985 | Wood et al. |
| 4,534,282 A | 8/1985 | Marinoza |
| 4,535,247 A | 8/1985 | Kurtz |
| 4,601,822 A | 7/1986 | Zamburro |
| 4,643,464 A | 2/1987 | Weinhold |
| 4,766,321 A | 8/1988 | Lew et al. |
| 4,769,131 A | 9/1988 | Noll et al. |
| 4,786,812 A | 11/1988 | Humphreys |
| 4,831,268 A | 5/1989 | Fisch et al. |
| 4,866,282 A | 9/1989 | Miripol et al. |
| 4,871,559 A | 10/1989 | Dunn et al. |
| 4,887,008 A | 12/1989 | Wood |
| 4,887,192 A | 12/1989 | Simpson et al. |
| 4,902,411 A | 2/1990 | Lin |
| 4,919,951 A | 4/1990 | Jensen et al. |
| 4,948,980 A | 8/1990 | Wedekamp |
| 4,971,687 A | 11/1990 | Anderson |
| 5,023,460 A | 6/1991 | Foster, Jr. et al. |
| 5,037,618 A | 8/1991 | Hager |
| 5,048,404 A | 9/1991 | Bushnell et al. |
| 5,069,782 A * | 12/1991 | Moyher et al. ............... 210/192 |
| 5,120,450 A | 6/1992 | Stanley, Jr. |
| 5,151,252 A | 9/1992 | Mass |
| 5,208,461 A | 5/1993 | Tipton |
| 5,227,637 A | 7/1993 | Herold et al. |
| 5,230,792 A | 7/1993 | Sauska et al. |
| 5,235,905 A | 8/1993 | Bushnell et al. |
| 5,247,178 A | 9/1993 | Ury et al. |
| 5,288,647 A | 2/1994 | Zimlich, Jr. et al. |
| 5,302,356 A | 4/1994 | Shadman et al. |
| 5,393,541 A | 2/1995 | Bushnell et al. |
| 5,395,591 A | 3/1995 | Zimlich, Jr. et al. |
| 5,446,289 A | 8/1995 | Shodeen et al. |
| 5,447,733 A | 9/1995 | Bushnell et al. |
| 5,451,367 A | 9/1995 | Stark et al. |
| 5,489,442 A | 2/1996 | Dunn et al. |
| 5,498,394 A | 3/1996 | Matschke |
| 5,573,666 A | 11/1996 | Korin |
| 5,597,482 A | 1/1997 | Melyon |
| 5,626,768 A | 5/1997 | Ressler et al. |
| 5,658,530 A | 8/1997 | Dunn |
| 5,686,789 A | 11/1997 | Schoenbach |
| 5,768,853 A | 6/1998 | Bushnell |
| 5,786,598 A | 7/1998 | Clark et al. |
| 5,814,523 A | 9/1998 | Zimlich, Jr. et al. |
| 5,843,309 A | 12/1998 | Mancil |
| 5,900,211 A | 5/1999 | Dunn et al. |
| 5,916,439 A | 6/1999 | Oleskow |
| 5,925,885 A | 7/1999 | Clark et al. |
| 5,939,829 A | 8/1999 | Schoenbach |
| 6,013,918 A | 1/2000 | Bushnell |
| 6,027,754 A | 2/2000 | Bushnell et al. |
| 6,030,578 A | 2/2000 | McDonald |
| 6,045,845 A | 4/2000 | Gundt |
| 6,054,097 A | 4/2000 | Mass et al. |
| 6,072,273 A | 6/2000 | Schoenbach |
| 6,083,387 A | 7/2000 | Le Blanc et al. |
| 6,087,783 A | 7/2000 | Eastlund et al. |
| 6,110,423 A | 8/2000 | Bushnell et al. |
| 6,150,663 A | 11/2000 | Rosenthal |
| 6,190,609 B1 | 2/2001 | Chapman et al. |
| 6,228,332 B1 | 5/2001 | Dunn et al. |
| 6,312,931 B1 | 11/2001 | O'Dwyer et al. |
| 6,346,770 B1 | 2/2002 | Schoenbach |
| 6,433,344 B1 | 8/2002 | Salisbury |
| 6,566,659 B1 | 5/2003 | Clark et al. |
| 6,589,489 B2 | 7/2003 | Morrow et al. |
| 6,614,039 B2 | 9/2003 | Hollander |
| 6,730,923 B1 | 5/2004 | May et al. |
| 6,849,233 B2 | 2/2005 | Bushnell et al. |
| 7,038,219 B2 | 5/2006 | Clark et al. |
| 7,091,495 B2 * | 8/2006 | Panico et al. ............. 250/432 R |
| 7,511,281 B2 | 3/2009 | Cooper |
| 2002/0043504 A1 * | 4/2002 | Chen et al. ................... 210/748 |
| 2002/0103409 A1 | 8/2002 | Kuriyama |
| 2002/0119072 A1 | 8/2002 | Bushnell et al. |
| 2002/0168305 A1 | 11/2002 | Morrow et al. |
| 2002/0176796 A1 | 11/2002 | Holloway et al. |
| 2003/0030011 A1 | 2/2003 | Brown et al. |
| 2003/0060747 A1 | 3/2003 | Fries et al. |
| 2003/0147770 A1 | 8/2003 | Brown et al. |
| 2004/0004044 A1 | 1/2004 | Anderson |
| 2004/0144733 A1 | 7/2004 | Cooper |
| 2004/0166018 A1 | 8/2004 | Clark |
| 2005/0109690 A1 | 5/2005 | Bechtold |
| 2005/0115498 A1 | 6/2005 | Ingram et al. |
| 2005/0264236 A1 | 12/2005 | Lloyd et al. |
| 2007/0045561 A1 | 3/2007 | Cooper |

FOREIGN PATENT DOCUMENTS

| | | |
|---|---|---|
| DE | 19617467 A1 | 11/1997 |
| EP | 0277505 | 8/1988 |
| EP | 1069444 | 1/2001 |
| EP | 2485038 | 8/2012 |
| FR | 2879588 A1 | 6/2006 |
| JP | 49119441 | 10/1974 |
| JP | 50026255 | 3/1975 |
| JP | 51106236 | 8/1976 |
| JP | 58214388 | 12/1983 |
| JP | 02095585 | 7/1990 |
| JP | 03015692 | 2/1991 |
| JP | 06048882 U | 7/1994 |
| JP | 06233979 | 8/1994 |
| JP | 07213643 | 3/1995 |
| JP | 08117741 | 5/1996 |
| JP | 2001500782 | 1/2001 |
| JP | 2001-066422 | 3/2001 |

(56) References Cited

FOREIGN PATENT DOCUMENTS

| | | |
|---|---|---|
| JP | 200441222 | 2/2004 |
| JP | 2004121577 | 4/2004 |
| JP | 2005152708 | 6/2005 |
| JP | 2005527953 A | 9/2005 |
| JP | 2006082085 | 3/2006 |
| JP | 2007502200 | 2/2007 |
| JP | 2007533441 A | 11/2007 |
| JP | 3141893 | 4/2008 |
| JP | 2008299094 A | 12/2008 |
| JP | 2009508663 | 3/2009 |
| WO | WO-9714915 | 4/1997 |
| WO | WO-9950183 | 10/1999 |
| WO | WO-0078681 | 12/2000 |
| WO | WO-0078681 A2 | 12/2000 |
| WO | 03004579 A1 | 1/2003 |
| WO | WO-2004050130 | 6/2004 |

OTHER PUBLICATIONS

Aquafine Wedeco Environmental Systems Inc. "Water Disinfection with Ultraviolet Light" 1996, 22 pp.
Bender, "Photolytic oxidation of contaminated water using a high-energy, pulsed ultra-violet flashlamp operating in the blackbody regime." OSA Symposium. 1997, pp. 1-14.
Dunn, "PureBright: Sterilization Using Intense Pulsed Light" Summary of Presentation to International Society of Pharmaceutical Engineers Dec. 1995, 11 pp.
Jagger, "Introduction to Research in Ultraviolet Photo Biology" 1967, pp. 1-164.
Rentschler, et al. "Bactericidal Effect of Ultraviolet Radiation" Research Department, Westinghouse Lamp Division, Bloomfield, New Jersey pp. 745-774.
Zimmerman, et al. "Electrical Breakdown, Electropermeabilization and Electrofusion" Physiology Biochemistry Pharmacology. vol. 105 1986, pp. 176-256.
Bolton, Jr. Ultraviolet applications Handbook, 2nd Edition 2001, Photosciences Inc., p. 37.
PCT International Search Report and Written Opinion of the International Searching Authority from PCTUS0631643 dated Jan. 16, 2008.
Notice of Allowance for U.S. Appl. No. 11/217,772 mailed Nov. 18, 2008.
"Landfill Systems", *Aquafine Wedeco Environmental Systems*, Inc. 1996.
Cooper, "U.S. Appl. No. 11/217,772"
U.S.P.T.O., Office Action from U.S. Appl. No. 11/217,772 mailed Jun. 25, 2008.
Examination Report from the European Patent Office for EP App. No. 068014273 dated Mar. 5, 2010.
Bakthisaran, "The Application of UV Technology to Pharmaceutical Water Treatment", European Journal of Parenteral Sciences 3(4) Mar. 1998, pp. 97-102.
Cooper, "U.S. Appl. No. 11/217,772, filed Aug. 31, 2005".
Rentschler, "Bactericidal Effect of Ultraviolet Radiation", Research Department, Westinghouse Lamp Division, Bloomfield, New Jersey Oct. 26, 1940 , 745-774.
International Search Report and Written Opinion of the International Searching Authority for PCT US2008086305 mailed Jun. 29, 2009.
Office Action from the Mexican Patent Office in the Mexican Institute of Industrial Property for Mexican application No. MXa2008003022 issued Aug. 19 2010.
International Search Report and Written Opinion of the International Searching Authority for PCT/US2010/029251 mailed Nov. 26, 2010.
Non Final Office Action from U.S. Appl. No. 12/416,075 mailed Dec. 7, 2010.
Notice of First Office Action from the State Intellectual Property Office of the People's Republic of China for App. No. 2006800369594 dispatched Oct. 21, 2010.
Notice of Rejection from the Japan Patent Office for App. No. 2008529088 dated Feb. 8, 2011.
Office of Intellectual Property Austrailia, Examiner's First Report on App. No. 2006285220 dated Jan. 18, 2011.
Australian Patent Application No. 2006285220, Ultraviolet Sciences, Inc. Notice of Acceptance dated Oct. 30, 2012, 3 pages.
Notice of Final Decision of Rejection from the Japan Patent Office for Japanese Patent App. No. 2008-529088 mailed Jun. 1, 2012.
Decision on Rejection from the Patent Office of the State Intellectual Property Office of the People's Republic of China for Application No. 200680036959.4 mailed Jul. 4, 2012.
Office Action for Japanese Patent Application No. 2010-539632 mailed by the Japanese Patent Office on Jul. 31, 2012.
Patent Examination Report No. 2 for Patent Application No. 2006285220 issued by the Australian Patent Office on Aug. 2, 2012.
Patent Abstracts for Japanese Publication No. 2004-121577 dated Apr. 22, 2004 with translation.
Patent Abstracts for Japanese Publication No. 07-213643 dated Aug. 15, 1995 with translation.
Extended European Search Report from European Application No. 10 762 191.4 mailed from the EPO on Oct. 17, 2012.
Non-final rejection from Korean Patent Application No. 2008-7007426 mailed from Korean Intellectual Property Office on Sep. 28, 2012.
Patent Examination Report No. 3 for Australian Patent Application No. 2006285220 mailed from the Australian Patent Office on Oct. 11, 2012.
Extended European Search Report from Application No. 12158784.4 mailed Jul. 5, 2012 (9 pages).
Final Office Action from U.S. Appl. No. 12/416,075 mailed Jul. 28, 2011 (17 pages).
Second Office Action from the State Intellectual Property Office of the People's Republic of China for App. No. 2006800369594 dated Nov. 8, 2011 (8 pages).
Patent Examination Report No. 1 from Australian Patent Application No. 2008338653 mailed from Australian Patent Office on Feb. 5, 2013.
Non-Final Office Action from U.S. Appl. No. 11/959,445 mailed Jan. 9, 2013.
Notice of Allowance for Japanese Patent Application No. 2008-529088 mailed from the JPO on Jan. 15, 2013.
Notice of First Office Action for China Patent Application No. 201080023548.8 mailed from the Patent Office of the China State Intellectual Property Office on Dec. 28, 2012.
Communication Pursuant to Article 94(3) EPC for European Patent Application No. 12158784.4 mailed May 3, 2013, 6 pages.
Final Office Action for Japanese Patent Application No. 2010-539632 mailed by the Japan Patent Office on May 7, 2013, 5 pages.
Non-final office action from U.S. Appl. No. 12/416,075 mailed Aug. 6, 2013.
Notice on the Second Office Action for Chinese Patent Application No. 201080023548.8 mailed from the State Intellectual Property Office of the People's Republic of China on Jul. 15, 2013.
First Office Action from Canadian Patent Application 2,620,780 mailed from the Canadian Intellectual Property Office on Oct. 18, 2013.
Extended European Search Report from European Application No. 08860955.7 mailed Oct. 16, 2013.
Final office action from U.S. Appl. No. 12/416,075 mailed Dec. 19, 2013.
Non-Final Office Action for U.S. Appl. No. 12/416,075 mailed Jun. 5, 2014.
Decision on Rejection from the Patent Office of the State Intellectual Property Office of the People's Republic of China for Application No. 201080023548.8 mailed Jan. 30, 2014.
First Office Action for Japan Patent Application No. 2012-503626 mailed from the Japan Patent Office on Feb. 25, 2014.
Canadian Intellectual Property Office, Office Action dated Aug. 14, 2014 for Application No. 2,620,780 (2 pgs.).
Japan Patent Office Decision of Rejection dated Jul. 8, 2014 (4 pgs.).
Final Office Action, mailed Oct. 8, 2014 for U.S. Appl. No. 12/416,075 (14 pgs.).

(56) References Cited

OTHER PUBLICATIONS

Canadian Intellectual Property Office Second Office Action, mailed Aug. 14, 2014 for Canadian Patent Application 2,620,780 (3 pgs.).
Japan Patent Office Decision of Rejection, mailed Jul. 8, 2014 for Japanese patent Application No. 2010-539632 (4 pgs.).
European Patent Office Office Action, mailed Sep. 1, 2014 for European Patent Application No. 08860955.7 (4 pgs.).
Japan Patent Office Final Office Action, mailed Nov. 25, 2014 for Japanese Patent Application No. 2012-503626 (10 pgs.).
First Office Action for Japanese Patent Application No. 2010-539632 mailed by the Japan Patent Office on Jan. 27, 2015 (6 pgs.).
Invitation Pursuant to Rule 137(4) EPC for European Patent Application No. 12158784.4 mailed from the European Patent Office on Apr. 1, 2015 (2 pgs.).
Office Action for Korean Patent Application No. 10-2010-7015889 mailed from the Korean Intellectual Property Office on Apr. 14, 2015 (11 pgs.).
Notice on Reexamination for Chinese Patent Application No. 201080023548.8 mailed from the State Intellectual Property Office on May 8, 2015 (11 pgs.).
Examiner's Answer from U.S. Appl. No. 12/416,075 mailed Jun. 1, 2015 (14 pgs).
Decision of Dismissal of Amendment for Japanese Application No. 2012-503626 mailed from the Japan Patent Office on Apr. 28, 2015 (5 pgs.).

\* cited by examiner

ULTRAVIOLET LIGHT TREATMENT CHAMBER

BACKGROUND OF THE INVENTION

1. Field of the Invention

This invention relates generally to methods and apparatuses for the treatment of liquids and gases using ultraviolet light.

2. Discussion of the Related Art

Various approaches are used to reduce contamination in liquids and gases, such as in municipal drinking water supplies, ultrapure water systems for industrial processing and pharmaceutical manufacture, water and reagents for use in experimentation, gases used in sterile rooms, and the like. Such approaches are often used to reduce or eliminate the need for chemical aerosols, chemical preservatives, microfiltration, and like materials and processes for the treatment of liquids and/or gases.

An apparatus for irradiating media by means of a UV light external to a tubular body has been described, such as that described in U.S. Pat. No. 4,948,980, which is incorporated herein by reference. U.S. Pat. No. 4,948,980 provides an apparatus consisting of a tubular body through which medium to be irradiated flows, and at least two UV light sources with reflectors arranged externally to the tubular body and having parallel axes. The apparatus described in U.S. Pat. No. 4,948,980 relies on specular reflectors to control the uniformity of the light pattern delivered by the lamps. The lamp sources are relatively flat and aligned on their edges within the specular reflector in order to minimize the optical effects in the reflector. Unfortunately, U.S. Pat. No. 4,948,980 describes approaches that significantly limit the amount of dosage that can be provided to effectively treat a liquid or gas. For instance, U.S. Pat. No. 4,948,980 does not appreciate the use of a high reflectivity diffuse reflector to treat a liquid or gas with a low absorption cross section, nor, does the patent anticipate a large increase in dose delivered to a target as the net reflectivity of the entire chamber approaches 100 percent.

United States Patent Publication No. 2004/0166018, herein incorporated by reference, describes a UV air sterilization chamber comprising inner surfaces having a diffuse reflective behavior. The sterilization chamber includes an inlet aperture and an outlet aperture for air to flow through the chamber and a light source emitting a UV light. Unfortunately, the approaches described in US Patent Publication No. 2004/0166018 suffer from several problems. For example, since these approaches do not attempt to increase the transparent or translucent containment volume compared to total chamber volume, the performance of the apparatus is not maximized. In addition, the reflector used is not isolated from the medium being treated and there is no option to replace lamps without opening the chamber thereby increasing the difficulty in using and maintaining the system.

In U.S. Pat. No. 6,228,332, herein incorporated by reference, short-duration, high-intensity pulsed broad-spectrum polychromatic light is used to treat water for the deactivation of microorganisms. As described in U.S. Pat. No. 6,228,332, deactivation of microorganisms in water involves illuminating the water with at least one short-duration, high-intensity pulse of broad-spectrum polychromatic light. The system includes a watertight housing having an inlet port and an outlet port for the flow water. A tubular light source for deactivating microorganisms and a tubular baffle for directing the water flow are positioned within the watertight housing. Water enters the inlet port and flows between the watertight housing and the tubular baffle in one direction, around the end of the tubular baffle and back through the center of the tubular baffle in a second direction exiting the outlet port. In this case, water flows around the tubular light source which provides at least one short-duration, high-intensity pulse of broad-spectrum polychromatic light. However, the approaches described in this patent suffer from several problems. For example, the efficiency of the approaches described in U.S. Pat. No. 6,228,332 are limited because these approaches do not use a reflective surface or substantially enclose the treatment chamber in order to treat the liquid or gas target.

The present invention, in various embodiments, addresses the above and other needs and problems.

SUMMARY OF THE INVENTION

The present invention, in various embodiments, relates generally to methods and apparatuses for the treatment of liquids and gases using ultraviolet light. Approaches are described herein that advantageously allow for treating and/or reducing contamination in liquids and gases, such as in municipal drinking water supplies, ultrapure water systems for industrial processing and pharmaceutical manufacture, water and reagents for use in experimentation, gases used in sterile rooms, and the like. The approaches provide herein are easy to use and economical to implement, and provide higher effective treatment doses for the target liquid or gas for a given power input as compared with previous approaches. The approaches may be used to reduce or eliminate biological agents. Additionally, these approaches may be used to remove or eliminate or activate chemicals.

In one embodiment, an apparatus for the treatment of a liquid includes a chamber having at least one inner surface. The chamber is at least 80 percent enclosed. The apparatus also includes an ultraviolet (UV) transmissive tube, which is disposed within the chamber and is adapted for the passage of the liquid (or gas) therethrough. The apparatus further includes a UV lamp and the UV lamp is disposed within the UV transmissive tube. A reflective material is interspersed between the chamber and the transmissive tube, and the reflective material is adapted so as to reflect at least a portion of light emitted by the UV lamp. In one example, the reflective material is at least 80 percent reflective.

In many of these embodiments, the confluence of first light from the UV lamp and second light (and subsequent light) reflected from the reflective material produces an unexpectedly generally uniform light distribution to occur within a volume of the liquid. In other words, the light distribution using the present approaches is generally more uniform than expected and as compared to previous systems.

In others of these embodiments, increased fluence is achieved due to a better reflector or reflective surface when using highly transmissive liquids or gases. In this case, a substantial of the surface area (e.g., greater than 80%) surrounding the liquid is highly reflective.

In still other embodiments, increased uniformity and increased fluence are achieved. If the transmissivity of the liquid is substantially high, the increase in uniformity may occur but does impact performance as much as the increased fluence.

The reflective material may be disposed in a variety of different ways. In one example, the reflective material is disposed so as to line the inner surface of the chamber. In another example, the reflective material is mounted on the outer surface of the transmissive tube. In another example, the reflective material is disposed by coating the reflective material onto the inner surface of the chamber.

The UV lamp may also be disposed in a number of different configurations and positions. In one example, the UV lamp is disposed within a transmissive protective sleeve within the UV transmissive tube. Other configurations and placements of the UV lamp are possible.

Additionally, the reflective material may be composed according to a number of different formulations. For example, the reflective material may be polytetrafluoroethylene (PTFE), expanded polytetrafluoroethylene (ePTFE), coated aluminum, anodized aluminum, or polished aluminum. In addition, the reflective material may be a mixture of a binder and a reflecting additive. If a reflective additive is used, the reflecting additive may be barium sulfate, magnesium fluoride, magnesium oxide, aluminum oxide, titanium oxide, holmium oxide, calcium oxide, lanthanum oxide, germanium oxide, tellurium oxide, europium oxide, erbium oxide, neodymium oxide, samarium oxide, ytterbium oxide, or zirconium oxide.

The apparatus may also include an input and output port where the ultraviolet UV transmissive tube enters and exits the chamber. Each of the ports may assume a number of different configurations.

Additionally, the ultraviolet irradiance provided by the present approaches may fall into a variety of different ranges. In one example, the ultraviolet irradiance impinging on the liquid is in the range of about 0.01 W/cm.$^2$ and 20 W/cm$^2$. Other examples of ranges are possible.

BRIEF DESCRIPTION OF THE DRAWINGS

The above mentioned and other objects and features of the present embodiment and the manner of attaining them will become apparent, and the present embodiments themselves will be best understood by reference to the following description in conjunction with the accompanying drawings, wherein.

DETAILED DESCRIPTION OF THE PREFERRED EMBODIMENTS

The following is a description including the best mode presently contemplated for practicing the invention. This description is not to be taken in a limiting sense, but is made merely for the purpose of describing the general principles of the invention. The scope of the invention should be ascertained with reference to the issued claims.

The apparatus described herein provides for a large reduction in the total UV power required to treat a target liquid or gas to a specified dose level. This is accomplished by enclosing the target and the UV light source within a chamber which has walls with an extremely high reflectivity lining or coating and by minimizing the size and number of openings in the chamber wall and absorbing surfaces within the chamber. The chamber design allows for increased photon deposition resulting in enhanced UV irradiation efficiency. Synergy is achieved by combining both of these criteria because the dose delivered to the target increases exponentially as the chamber wall reflectivity and the percentage of the chamber enclosed approach 100 percent. The resulting synergistic effect is more efficient than the singular effect of each of the criteria in sum. For example, a fully enclosed chamber with 99% reflective walls will deliver 10 times the dose to the target that an identical chamber with 90% reflective walls will.

Treatment of a liquid or gas within a transmissive tube to separate the liquid or gas from the chamber walls has advantages. Such a tube could be introduced into the chamber described above. In order to maximize the dose delivered to the target within the transmissive tube and transmissive media carrying the target inside the tube, the transmissive tube should enclose as much of the chamber volume as possible. This minimizes the amount of light which is reflected between walls without passing through the transmissive tube and into the target area.

Ultraviolet light, which has shorter wavelengths than visible light, is considered to include wavelengths measuring between 10 and 400 nm, generally corresponding to frequencies between $7.5 \times 10^{14}$ to $3 \times 10^{16}$ Hz. On the electromagnetic spectrum, ultraviolet light has wavelengths less than violet light in the visible spectrum and wavelengths greater than X rays. Ultraviolet light is divided into three categories, near ultraviolet (NUV), which is closest to visible light and consists of wavelengths from 400 to 300 nm; far ultraviolet (FUV), located after NUV and consists of wavelengths from 300 to 200 nm; and extreme ultraviolet (EUV) which is located after FUV and before X ray and consists of wavelengths from 200 to 100 nm. Ultraviolet light is also divided, based on biological effects, into UV-A (400 to 320 nm), UV-B (320 to 280 nm), and UV-C (280 to 100 nm) bands which do not directly correspond to the aforementioned designations.

While most UV irradiation processes can occur when stimulated by UV photons with wavelengths longer than 200 nm, many applications use sub-200 nm light to increase the process rates. In this regime, the efficiency of most light sources is relatively low. This low efficiency further drives the need for an efficient system to deliver the UV photons to their desired target.

Generally, methods and apparatuses for the treatment of liquids and gases using ultraviolet light are described herein below. Although the following description is particularly directed to the treatment of liquid and gaseous materials, it should be understood that the apparatus of the present embodiment may be easily adapted for the treatment of solid materials, such as particles in suspension or emulsions, foodstuffs, surgical instruments, and the like. For example, the treatment chamber may be adapted to remove the tubing material and input and output ports and replaced with a cavity for the placement of a solid material. This arrangement may render the treatment chamber fully or nearly fully enclosed. Besides solid materials, liquids and gases enclosed in a container, such as vials of reagents, pouches of blood and blood components, and other prepackaged liquids and gases may be treated using a slightly modified apparatus.

Ultraviolet light is useful for deactivating or killing microorganisms including bacteria, viruses, fungi, mold spores, protozoa, and the like biological materials. Deactivation is caused when ultraviolet radiation alters or mutates biomolecules such nucleic acids, i.e. deoxyribonucleic acid (DNA) and/or ribonucleic acid (RNA) and proteins, e.g. enzymes. When native DNA is exposed to a sufficient level of ultraviolet radiation, mutations are formed in the genetic material. The most common mutations are the 5,6-cyclobutyl dipyrimidines, pyrimidine dimers, pyrimidine adducts, pyrimidine hydrates, and DNA-protein crosslinks. Direct protein damage is less common but indirect damage of other biomolecules via proteins absorbing wavelengths greater than 290 nm is particularly relevant; proteins absorbent at these wavelengths generally contain tryptophan and tyrosine. In the presence of oxygen, energy transfer from the excited triplet state of tryptophan to oxygen occurs producing a singlet oxygen. Thus, tryptophan in protein acts as an endogenous photosensitizer in the UVB wavelength range by producing free radical oxygen, which reacts with proteins, unsaturated lipids, and bases in nucleic acids. In any case ultraviolet radiation promotes the generation of singlet oxygen and hydroxyl free radicals which can cause damage to cellular proteins, lipids, and carbohydrates.

Membraneous microorganisms are deactivated or killed when ultraviolet radiation penetrates the organism's membrane and alters its genetic material and, to a lesser extent, proteins (e.g. enzymes). In cases where an organism has sustained significant biomolecular damage, the microorganism may die. In cases where the genetic and/or proteinaceous material has been altered, but perhaps not completely destroyed, the microorganism may no longer be able to reproduce. Without the ability to reproduce, coupled with the short lifespan of most microorganisms, population size will diminish rapidly in material treated with ultraviolet radiation.

In the case of viruses, ultraviolet radiation mutates the genetic material such that the virus is no longer capable of infecting host cells and/or multiplying within a host organism using the host's cellular machinery. The UV dose for deactivating 99.99% of typical bacteria such as *Enterobacteria cloacae, Klebsiella pneumoniae, Pseudomonas aeruginosa, Salmonella typhimurium* A, *Vibrio cholerae*, and *Escherichia coli* is between 20 and 30 mJ/cm$^2$. For spore forming bacteria such as *Bacillus subtilis* in the sporulated state, the dose is higher, usually at least 60 mJ/cm$^2$. Deactivation of viruses such as polio and rotavirus requires a dose between 30 and 40 mJ/cm$^2$, but other viruses can require higher doses. Protozoa such as *Cryptosporidium parvum* and *Giardia muris* have been killed with doses as low as 10 mJ/cm$^2$ (*Ultraviolet Applications Handbook,* 2nd ed., James R. Bolton, Bolton Photosciences, Inc., 2001, p. 37).

Ultraviolet light is also used to decompose chemicals, particularly organic chemicals, into components which are safer or which can be more easily removed by activated carbon filtration, resin beds, or reverse osmosis, any of which are features which may be used in conjunction with the apparatus and methods described herein. This decomposition results from both direct photon absorption or by decomposition by OH— radicals which are produced in the proximity of the chemical molecule by the interaction of the ultraviolet light with water molecules or possibly other sources of OH— radicals. The decomposition may be also be achieved by using advanced oxidation methods such as adding ozone or hydrogen peroxide in combination with using ultraviolet light.

A table of dissociation wavelengths and the maximum wavelength which can cause this dissociation for common chemical bonds in organic substances is shown below.

| Dissociation Energies for Interatomic Bonds in Organic Substances | | |
|---|---|---|
| Chemical Bond | Dissociation Energy (UV Dose) [kcal/gmol] | Maximum Wavelength for Dissociation [nm] |
| C—C | 82.6 | 346.1 |
| C=C | 14.5 | 196.1 |
| C≡C | 199.6 | 143.2 |
| C—Cl | 81.0 | 353.0 |
| C—F | 116.0 | 246.5 |
| C—H | 98.7 | 289.7 |
| C—N | 72.8 | 392.7 |
| C=N | 147.0 | 194.5 |
| C≡N | 212.6 | 134.5 |
| C—O | 85.5 | 334.4 |
| C=O (aldehydes) | 176.0 | 162.4 |
| C=O (ketones) | 179.0 | 159.7 |
| C—S | 65.0 | 439.9 |
| C=S | 166.0 | 172.2 |
| H—H | 104.2 | 274.4 |
| N—N | 52.0 | 549.8 |
| N=N | 60.0 | 476.5 |
| N≡N | 226.0 | 126.6 |
| N—H (NH) | 85.0 | 336.4 |
| N—H (NH3) | 102.2 | 280.3 |
| N—O | 48.0 | 595.6 |
| N=O | 162.0 | 176.5 |
| O—O(O$_2$) | 119.1 | 240.1 |
| —O—O— | 47.0 | 608.3 |
| O—H (water) | 117.5 | 243.3 |
| S—H | 83.0 | 344.5 |
| S—N | 115.2 | 248.6 |
| S—O | 119.0 | 240.3 |

Source: "The application of UV technology to pharmaceutical water treatment," Bakthisaran, S., *European Journal of Parenteral Sciences,* 3(4), pp. 97-102, 1998.

Figure 1:
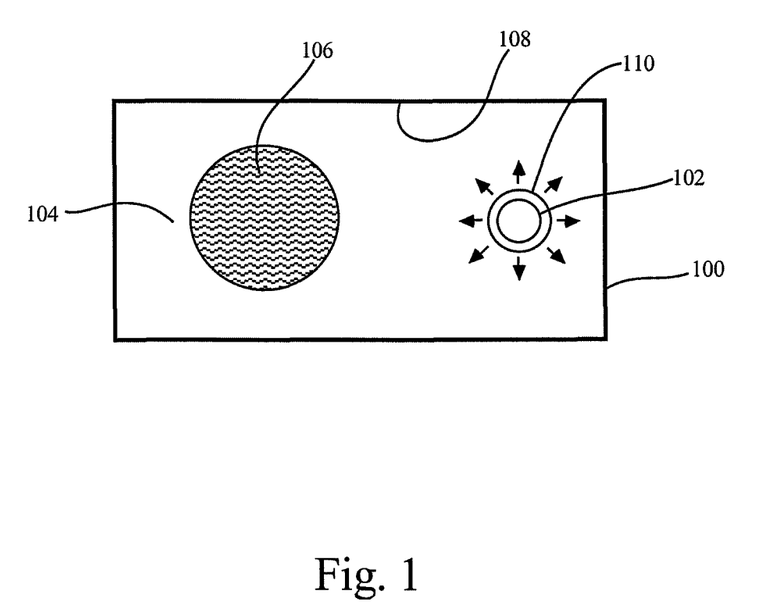
FIG. 1 is schematic showing one example of an ultraviolet light treatment system according to an embodiment of the present invention.
Figure 2:
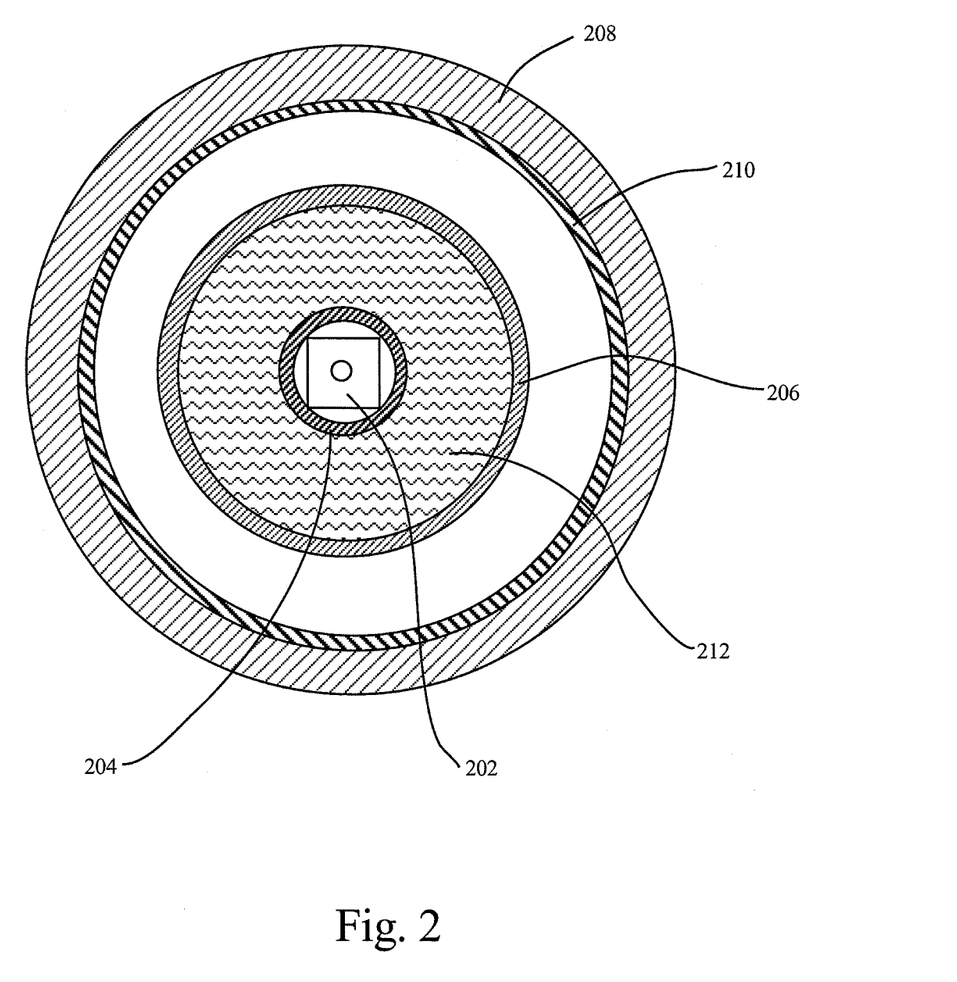
FIG. 2 is a schematic diagram of another example of an ultraviolet treatment system according to another embodiment of the present invention.
Figure 3:
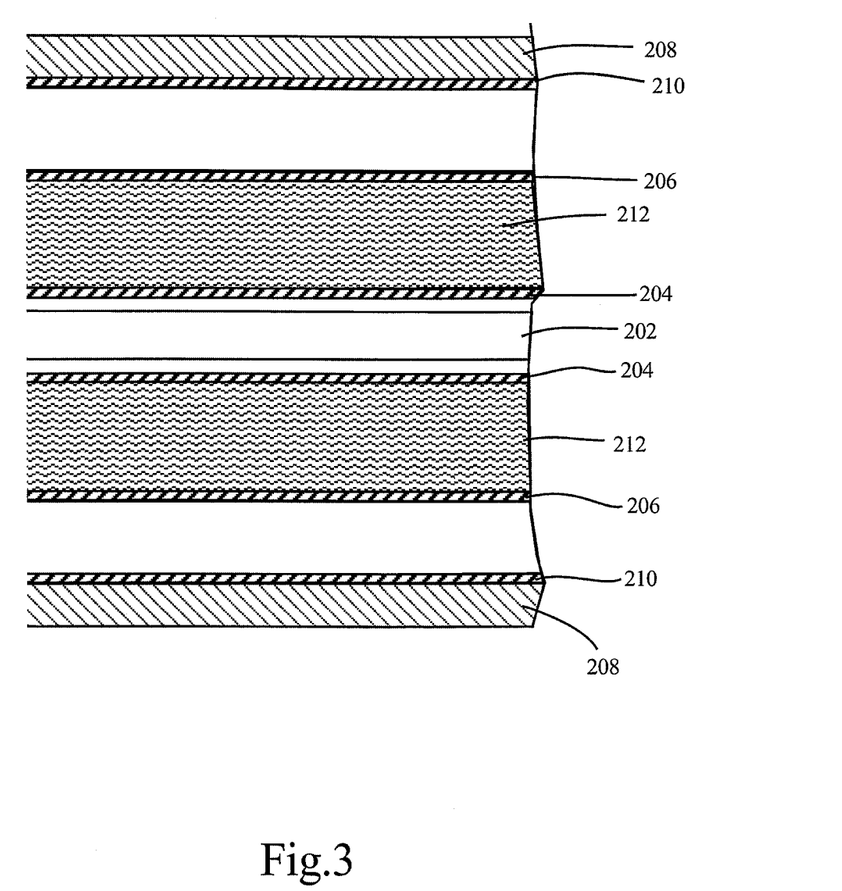
FIG. 3 is longitudinal cross section of the ultraviolet treatment system of FIG. 2 according to the other embodiment of the present invention.
Figure 4:
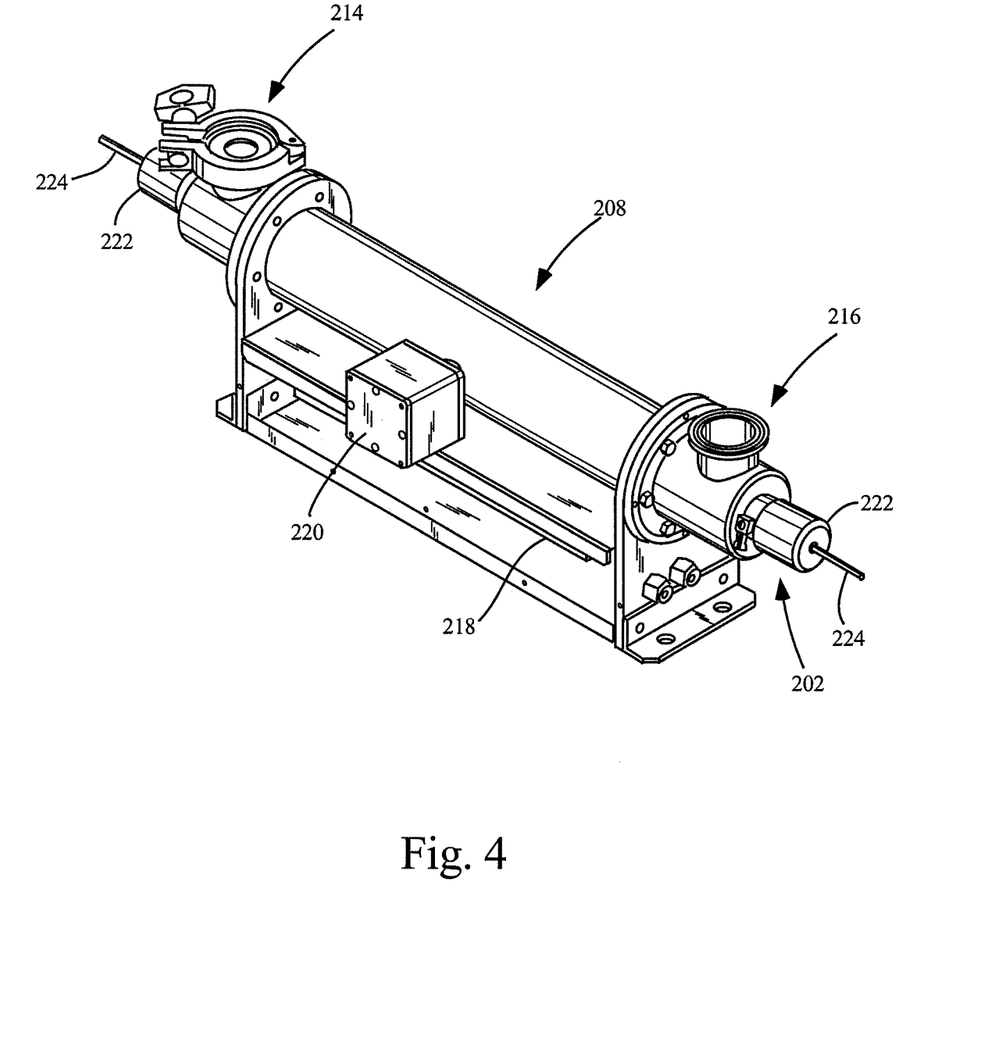
FIG. 4 is a perspective view the exterior of a treatment system of FIGS. 2 and 3 according to the other embodiment the present invention.
Figure 5:
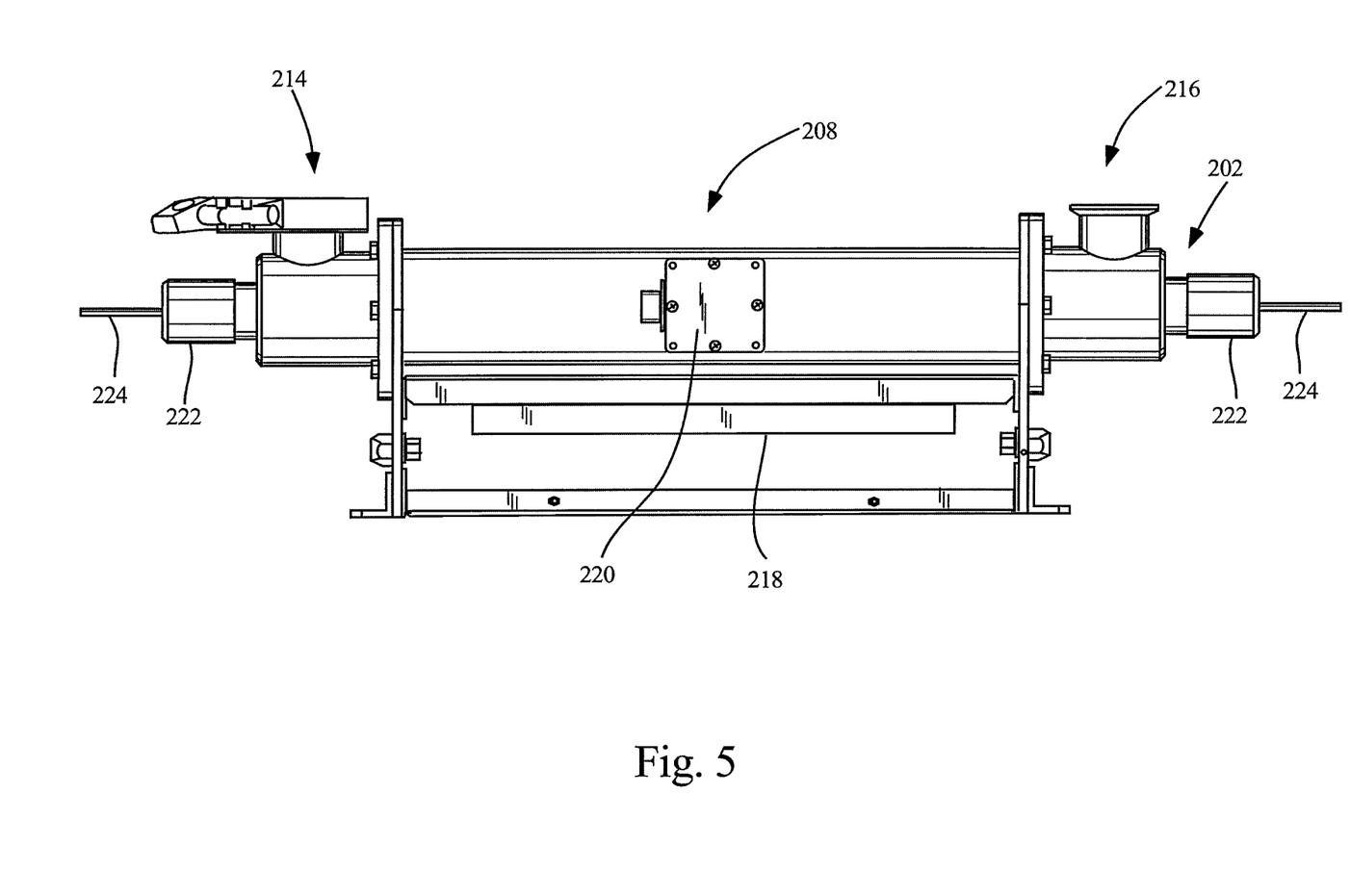
FIG. 5 is a side view of the ultraviolet treatment system of FIGS. 2-5 according to the other embodiment of the present invention.

Turning to FIG. 1, a representation of a treatment chamber is depicted. Shown are a chamber 100, an ultraviolet lamp 102, an ultraviolet transmissive tube 104, a liquid 106, a light reflective material 108, and an optional transmissive tube (or lamp sleeve) 110. Alternatively, the ultraviolet lamp may be enclosed within the ultraviolet transmissive tube 104. The chamber 100 contains an ultraviolet lamp 102 and a light transmissive tube 104. The ultraviolet lamp 102 may be enclosed by the optional transmissive tube 110. The chamber 100 may be coated or covered or lined with a light reflective material 108, as shown in FIG. 1. The ultraviolet lamp 102 may be located in a physically separate position, as shown in FIG. 1, from the ultraviolet transmissive tube 104. The light transmissive tube 104 runs through the chamber 100 where it is exposed to ultraviolet light provided by the ultraviolet lamp 102. The tube 104 may carry any type of liquid 106 or gas, including for example, water, air, experimental reagents, blood components (e.g. red blood cells, white blood cells, plasma) beverages for consumption, and the like. Therefore, as the liquid 106 passes through the ultraviolet transmissive tube 104, the liquid 106 is exposed to ultraviolet photons useful for the treatment of the liquid 106.

The chamber 100 of FIG. 1 has an input and output port (not shown) for an ultraviolet transmissive tube 104 to run through chamber 100. However, the input and output ports are fashioned as such to render the chamber 100 as substantially enclosed as possible. For example the input and/or output ports may utilize elbow, coiled, or other serpentine paths for gas and/or liquid flow to increase enclosure of the chamber. To further enhance enclosure, the flow path may be constricted to a smaller diameter and/or the reflector may be extended to a distance beyond the zone in which light is introduced. Additionally, certain features such as baffles may also be incorporated into the apparatus to optimize light containment within the chamber 100. In any case, any number and combination of the aforementioned techniques and devices may be used to increase chamber enclosure. As is further described hereinbelow, the apparatus reaches maximum efficiency when the chamber 100 approaches 100 percent enclosure and the reflective material approaches 100 percent reflectivity.

Although the chamber 100 depicted in FIG. 1 is coated with a reflective material 108, it should be understood that any type of reflective material or apparatus may be used. For example, the reflective material 108 which may be coated on the inside of the chamber 100 may be any of polytetrafluoroethylene (PTFE), expanded polytetrafluoroethylene (ePTFE), or other similar plastics; or coated, anodized, or polished aluminum. In another embodiment, the reflective material 108 may be a reflector such as a diffuse or specular reflector near but not necessarily attached to the chamber wall. Any type of specular reflector, in any type of shape, may be used with the present embodiment. In any form, the reflective material 108 should have a high level of reflectivity. In one embodiment, the reflectivity level of the reflective material 108 is in the range of 80 percent to 100 percent, and more preferably, 90 percent to 100 percent.

Although the exact percent reflectivity may change depending on the particular needs of an apparatus, it should be understood that the higher the reflectivity, the higher the efficiency of the treatment chamber. For example, a fully enclosed chamber comprising a material with a 90 percent reflectivity in comparison to a fully enclosed chamber comprising a reflective material with a 99 percent reflectivity will have a lower dose on the target. Assuming that the exemplary target and walls are the only absorbers in the chamber, on average a photon will be reflected back and forth 10 times more in the 99 percent reflective chamber than the 90 percent reflective chamber before being absorbed by the reflective material. Thus, the photons are 10 times more likely to be absorbed by the target in a 99 percent reflective chamber than the 90 percent reflective chamber when the chamber is entirely enclosed. Therefore, the 99 percent reflective chamber delivers 10 times the ultraviolet light dose on the target as the 90 percent reflective chamber.

Similarly, a 99 percent enclosed chamber will deliver a higher ultraviolet light dose on a target than a 90 percent enclosed chamber. In a less enclosed chamber, photons are more likely to be reflected out of the chamber, thus reducing the likelihood of the photons being absorbed by the target. As such, the dosage of ultraviolet light treatment ultimately delivered to a target material is inversely related to absorbance where reflectivity of the apparatus components and enclosability of the chamber affects absorbance.

The ultraviolet lamp 102 may be of any type useful for providing ultraviolet radiation. For example, low pressure mercury lamps, medium pressure mercury lamps, excimer lamps, flashlamps with xenon and other fill mixtures, and microwave-driven lamps may be used with the present embodiment. The ultraviolet lamp provides at least one wavelength less than 400 nm to a target for the deactivation or killing of biological materials, direct destruction of chemicals, and indirect destruction of chemicals through advanced oxidation using oxidizing agents such as $H_2O_2$ and $O_3$ therein. The ultraviolet lamp 102 may be enclosed by the optional transmissive tube 110 which allows a technician to change out the lamp without opening the main chamber. Such a tube is optional and may be applied to the present embodiment for ease of operation; however, the present embodiment will function with out the lamp sleeve 110.

The ultraviolet transmissive tube 104 may be of any material that is substantially transmissive to ultraviolet light. To achieve maximum efficiency of the treatment chamber, it is preferable for the ultraviolet transmissive tube material to near 100 percent transmissivity as possible. In cases where 100 percent transmissivity is not possible, materials such as fused silica (Heraeus Heralux, Momentive 214), synthetic quartz (Heraeus Suprasil, Momentive 021 and 022), fluorine doped silica (Asahi Glass AQX), and sapphire (Saphikon EFG sapphire), being generally higher than 80 percent transmissive in the wavelengths below 300 nm, are useful.

Other examples of configurations for systems of treating liquids are shown in co-pending U.S. application Ser. No. 11/217,772 entitled "ULTRAVIOLET LIGHT TREATMENT CHAMBER" and which is incorporated here by reference in its entirety.

Referring now to FIGS. 2-5, another example of a system for the ultraviolet (UV) treatment of liquids or gases is described. The system includes a lamp 202, which is encased within an inner sleeve 204. The inner sleeve 204 is itself enclosed in a transmissive tube 206 (or a protective layer) and the transmissive tube 206 is disposed within a treatment chamber 208. The treatment chamber 208 has a reflective material 210 interspersed between the transmissive tube 206 and the treatment chamber 208. In this example, the reflective material 210 is disposed on its inner surface. In addition, reflective material 210 may be disposed on the outer surface of the transmissive tube 206. Alternatively, the reflective material 210 may be attached to the transmissive tube 206 or the reflective material 210 may be a freestanding structure. Other placements and configurations for the reflective material 210 are possible. A liquid or gas 212 passes through the transmissive tube 206. In one example, the treatment chamber 208 is at least 80 percent enclosed.

The transmissive tube 206 runs through the chamber 208 where it is exposed to ultraviolet light provided by the ultraviolet lamp 202. The tube 206 may carry any type of liquid or gas 212, including for example, water, air, experimental reagents, blood components (e.g. red blood cells, white blood cells, plasma) beverages for consumption, and the like. Therefore, as the liquid or gas 212 passes through the ultraviolet transmissive tube 206, the liquid 212 (or gas) is exposed to ultraviolet photons useful for treating the liquid or gas 212 (and/or items within the liquid or gas 212). A UV monitor 220 monitors the level of UV radiation in the treatment chamber 208.

The treatment chamber 208 has an input port 214 and an output port 216 that allow for the ultraviolet transmissive tube 206 to run through the chamber 208. In other examples, the roles of the input port 214 and output port 216 are reversed. The input port 214 and the output port 216 are fashioned as such to render the chamber 208 as substantially enclosed as possible. For example the input port 214 and/or output port 216 may utilize elbow, coiled, or other serpentine paths for gas and/or liquid flow to increase enclosure of the chamber 208. To further enhance enclosure, the flow path may be constricted to a smaller diameter and/or the reflective material 210 may be extended to a distance beyond the zone in which light is introduced. Additionally, additional structures such as baffles may also be incorporated into the apparatus to optimize chamber concealment. In any case, any number and combination of the aforementioned techniques, structures, and devices may be used to increase chamber enclosure.

Although the chamber 208 depicted in FIGS. 2-5 is coated with a reflective material 210, it should be understood that any type of reflective material 210 or reflective structure may be used. For example, the reflective material 210 which may be coated or lined on the inside of the chamber 208 may be a material such as polytetrafluoroethylene (PTFE), expanded polytetrafluoroethylene (ePTFE), or other similar plastics; or coated, anodized, or polished aluminum. In another example, the reflective material 210 may be a reflector such as a diffuse or specular reflector. Any type of specular reflector, in any type of shape, may be used with the present example. In many examples, the reflective material 210 has a high level of reflectivity. For instance, the reflectivity level of the reflective material 210 may be in the range of 80 percent to 100 percent, and some approaches are 90 percent to 100 percent.

Although the exact percent reflectivity of the reflective material 210 may change depending on the particular needs of an apparatus, it should be understood that the higher the reflectivity, the higher the efficiency of the treatment chamber 208. For example, a fully enclosed chamber comprising a material with a 90 percent reflectivity in comparison to a fully enclosed chamber comprising a reflective material with a 99 percent reflectivity will have a lower dose on the target. Assuming that the exemplary target and walls are the only absorbers in the chamber, on average a photon will be reflected back and forth 10 times more in the 99 percent reflective chamber than the 90 percent reflective chamber before being absorbed by the reflective material. Thus, the photons are 10 times more likely to be absorbed by the target in a 99 percent reflective chamber than the 90 percent reflective chamber when the chamber is entirely enclosed. Therefore, the 99 percent reflective chamber delivers 10 times the ultraviolet light dose on the target as the 90 percent reflective chamber.

Similarly, a 99 percent enclosed chamber will deliver a higher ultraviolet light dose on a target than a 90 percent enclosed chamber. In a less enclosed chamber, photons are more likely to be reflected out of the chamber, thus reducing the likelihood of the photons being absorbed by the target. As such, the dosage of ultraviolet light treatment ultimately delivered to a target material is inversely related to absorbance where reflectivity of the apparatus components and enclosability of the chamber affects absorbance.

The ultraviolet lamp 202 may be of any type useful for providing ultraviolet radiation. For example, low pressure mercury lamps, medium pressure mercury lamps, excimer lamps, flashlamps with xenon and other fill mixtures, and microwave-driven lamps may be used. Other examples of lamps are possible. In one example, the ultraviolet lamp 202 provides at least one wavelength less than 400 nm to a target for the deactivation or killing of biological materials therein. In another example, the ultraviolet lamp 202 provides at least one wavelength less than 400 nm to a target for the destruction of chemical compounds. The ultraviolet lamp 202 is connected to a power cable 224 in order to receive power. Additionally, end caps 22 may cover the ends of the lamp 202 to provide protection for the lamp 202. Furthermore, a lamp ballast 208 is also provided to, for example, limit current for the lamp 202.

Furthermore, an additional structure or layer exterior to the reflective material 210 may be provided to protect the reflective material 210, contain pressure, or both. Additionally, the transmissive tube 206 (or a protective layer) may contain system pressure.

As mentioned, the ultraviolet lamp 202 is enclosed by the inner sleeve 204, which allows a technician to change out the lamp 202 without opening the chamber 208. The inner sleeve 204 and the ultraviolet transmissive tube 206 may be of any material that is substantially transmissive to ultraviolet light. To achieve maximum efficiency of the treatment chamber 208, in some approaches, the material used for the inner sleeve 204 and the transmissive tube 206 is near 100 percent transmissivity as possible. In cases where 100 percent transmissivity is not possible, materials such as fused silica (Heraeus Heralux, Momentive 214), synthetic quartz (Heraeus Suprasil, Momentive 021 and 022), fluorine doped silica (Asahi Glass AQX), and sapphire (Saphikon EFG sapphire), being generally higher than 80 percent transmissive in the wavelengths below 300 nm, are useful Due to the high reflectivity of the reflective material 210 in the present example, the vast majority of the ultraviolet photons are deposited into the liquid or gas (and/or to items within the liquid or gas 212) instead of the walls of the chamber 208. Consequently, the liquid or gas 212 (and/or items in the liquid or gas 212) receive a higher effective dose of radiation for a given input power.

Due to the lack of losses in other parts of the system, the upper limit to the number of photons that are absorbed by the liquid or gas 212 (and/or items within the liquid or gas 212) is multiplied by a factor roughly equal to the ratio of losses of the wall material of the chamber 208 (e.g., as low as 1 percent) to that of stainless steel (e.g., 40 percent). The exact increase in UV dosage is affected by a variety of factors such as the number and size of penetrations into the volume containing the ultraviolet lamp 202 and liquid or gas 212, and any other disruptions in the surface of the reflective material 210. The overall increase in dosage over previous semi-reflective chambers (e.g., stainless steel chambers) is significant.

As mentioned, increased fluence may also be achieved due to a better reflector or reflective surface when using highly transmissive liquids. In this case, a substantial of the surface area (e.g., greater than 80%) surrounding the liquid is highly reflective.

In still other examples, increased uniformity and increased fluence are achieved. If the transmissivity of the liquid is substantially high, the increase in uniformity may occur but does impact performance as much as the increased fluence.

The increased dosage described above is accompanied by an unexpected increase in uniformity of the dose throughout the chamber, when compared to a system with a semi-reflective chamber wall. Normally, with higher fluence, a decrease in uniformity is expected, but the effect of minimizing the photon losses other than within the target gas or liquid produces a more uniform deposition of those photons within the target. This effect is essentially independent of geometry and primarily depends on the total reflectivity of the chamber walls or enclosure and on the transmissivity of the components involved.

A separate uniformity-enhancing effect which occurs for a different reason than the one above arises under certain conditions in this chamber. This effect is dependent upon the geometry of the chamber. It is also important only over a range of transmissivities of the liquid or gas 212. If the transmissivity of the liquid or gas 212 exceeds 90-95% (attenuation of 5-10%) over the distance from the light source to the chamber wall, then the effect described above does much more to create an unexpected uniformity of fluence in the chamber, and the effect described below is negligible. If the transmissivity is less than 5-10% (attenuation of 90-95%) over the distance from the light source to the chamber wall, then a very small amount of light reaches the chamber wall and once again the effect described below is negligible. For the range of transmissivities in the liquid or gas 212 such that the attenuation falls between nominally 5% and 95%, the effect described below is important in providing more uniform fluence to the target.

Further, the ultraviolet irradiance provided by the present approaches may fall into a variety of different ranges. In one example, the ultraviolet irradiance impinging on the liquid is in the range of about 0.01 W/cm.$^2$ and 20 W/cm$^2$. Other examples of ranges are possible.

Figure 6:
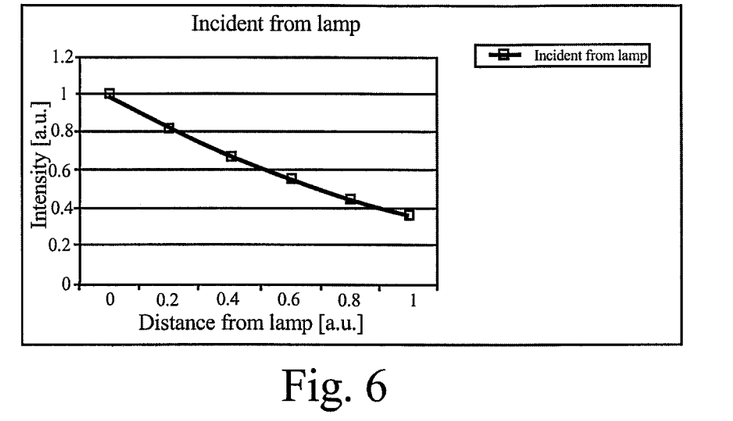
FIGS. 6-8 are charts showing light absorption properties of an ultraviolet light treatment system according to various embodiments of the present invention.
Figure 7:
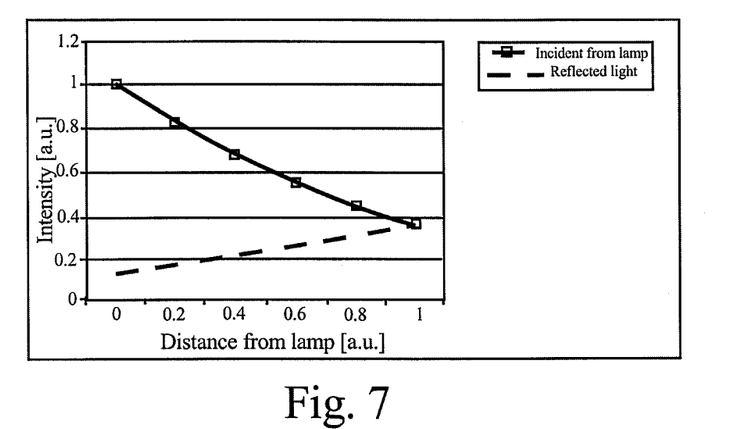
Figure 8:
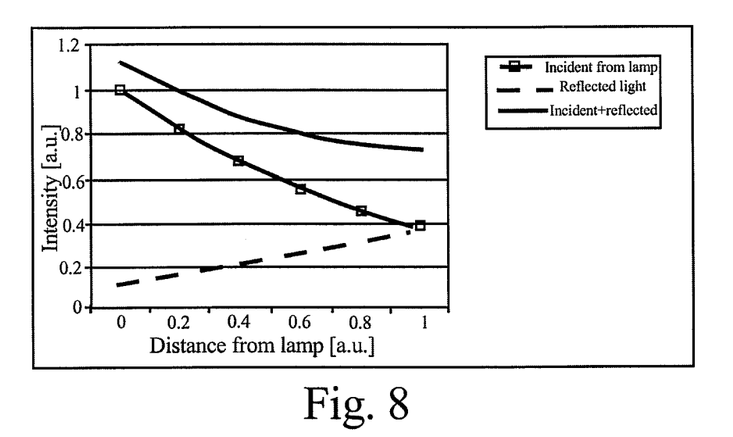

Referring now to FIGS. 6-8, the light absorption properties of the some of the systems described herein are described. The intensity of light which is transmitted through an absorbing medium is governed by Beer's Law:

$$I=I_o e^{-\alpha x}$$

where $I_o$ is the initial intensity, x is the distance traveled through the absorbing medium, e is the base of natural logarithms (e=2.718282) and α is an attenuation constant determined by the characteristics of the medium. If the medium and its dimensions are such that only a significant fraction of the light is absorbed after a single pass through the medium, then the effect shown in FIGS. 6-8 occurs.

FIG. 6 plots the intensity of light that enters the medium (Distance=0) to a particular distance x into the medium (Distance=1, with arbitrary units) at which the intensity is 1/e (e.g., approximately ⅓) of the incident intensity. If there is a non-reflecting surface at x, then the remaining light is absorbed and the difference in intensity (and therefore, the dose) between Distance=0 and Distance=x is 2.72.

FIG. 7 shows the same situation, but with a 100% reflector replacing the non-reflective surface at Distance=x. The reflected light is attenuated at the same rate as the incident light as it travels back through the medium. The intensity of light at a given distance is approximately the sum of the incident and the reflected light. For simplicity, any reflected light from the surface at Distance=0 is neglected. In many applications, that light would be reabsorbed or transmitted away, so neglecting it is a good approximation in many circumstances.

The intensity due to the sum of these two curves is shown in FIG. 8. In this case, the peak intensity is higher (1.14 vs. 1.00) and, in addition, the difference in intensity between Distance=0 and Distance=x is 1.54. This example shows that the intensity is much more uniform throughout the medium due to the presence of the reflective material. The improvement in uniformity of intensity (and therefore, the dose) is more than 70% for this example. The improvement in uniformity in intensity results in higher treatment efficiency and a lower peak intensity (less overdosing) to achieve a given dose in the media, both of which are significant improvements over prior reflectorless systems. In other words, FIG. 8 shows the generally uniform light distribution properties of the present approaches described herein.

Those skilled in the art will recognize that a wide variety of modifications, alterations, and combinations can be made with respect to the above described embodiments without departing from the spirit and scope of the invention, and that such modifications, alterations, and combinations are to be viewed as being within the scope of the invention. All references cited herein are incorporated by reference.

What is claimed is:

1. An apparatus for the treatment of a fluid, the apparatus comprising:
    a chamber, at least 80 percent of the chamber being enclosed by at least one wall having an inner surface, the inner surface of the at least one wall enclosing the chamber being covered by a light reflective material that is at least 80 percent reflective;
    an ultraviolet-transmissive tube including an interior and a continuous interior-facing surface surrounding the interior, the ultraviolet-transmissive tube being made of a material that is transmissive to ultraviolet light, the ultraviolet-transmissive tube being disposed within the chamber and adapted to permit the fluid to pass through the chamber by flowing through the interior of the ultraviolet-transmissive tube, wherein the fluid in the chamber is fully contained by the continuous interior-facing surface within the interior of the ultraviolet-transmissive tube;
    an ultraviolet lamp, the ultraviolet lamp being disposed within a transmissive protective sleeve positioned within the interior of the ultraviolet-transmissive tube and continuously surrounded by the interior-facing surface of the ultraviolet-transmissive tube.

2. The apparatus of claim 1, wherein the transmissivity of the liquid is such that its attenuation falls in a range of approximately 5 percent to approximately 95 percent.

3. The apparatus of claim 1, wherein the reflective surface comprises a reflective material comprising at least one material selected from a group consisting essentially of polytetrafluoroethylene (PTFE), expanded polytetrafluoroethylene (ePTFE), coated aluminum, anodized aluminum, and polished aluminum.

4. The apparatus of claim 1, wherein the reflective material comprises a reflective material comprising a mixture, the mixture comprising a binder and a reflective additive.

5. The apparatus of claim 4, wherein the reflective additive comprises at least one material selected from a group consisting essentially of barium sulfate, magnesium fluoride, magnesium oxide, aluminum oxide, titanium oxide, holmium oxide, calcium oxide, lanthanum oxide, germanium oxide, tellurium oxide, europium oxide, erbium oxide, neodymium oxide, samarium oxide, ytterbium oxide, and zirconium oxide.

6. The apparatus of claim 1, wherein the chamber comprises an input port and an output port for accommodating the ultraviolet-transmissive tube.

7. The apparatus of claim 1, wherein an ultraviolet irradiance impinging on the fluid comprises a range of approximately 0.01 W/cm$^2$ to approximately 20 W/cm$^2$.

8. The apparatus of claim 1, wherein 80-99 percent of the inner surface of the at least one wall enclosing the chamber is covered by the light reflective material.

9. The apparatus of claim 1, wherein the ultraviolet-transmissive tube has a continuous exterior-facing surface opposite the continuous inner-facing surface, the continuous exterior-facing surface having reflective material disposed thereon.

10. The apparatus of claim 1, wherein the continuous inner-facing surface of the ultraviolet-transmissive tube is configured to permit at least one of water, blood, one or more blood components, and beverage to flow through the interior of the ultraviolet-transmissive tube while being contained by the continuous interior-facing surface within the interior of the ultraviolet-transmissive tube.

11. The apparatus of claim 6, wherein a first end of the ultraviolet lamp passes through the input port and projects from an interior of the chamber and a second end of the ultraviolet lamp passes through the output port and projection from the interior of the chamber.

12. The apparatus of claim 1, wherein the light reflective material is at least 90% reflective.

13. The apparatus of claim 1, wherein the fluid is contained in the interior of the ultraviolet-transmissive tube between the continuous interior-facing surface surrounding the interior of the ultraviolet-transmissive tube and an exterior-facing surface of the transmissive protective sleeve positioned within the interior of the ultraviolet-transmissive tube.

* * * * *